United States Patent [19]

Etes

[11] 4,153,055
[45] May 8, 1979

[54] PLASTIC COMPOSITION MANUFACTURE THEREOF, AND PAD FORMED THEREWITH

[75] Inventor: Donald E. Etes, Crystal Lake, Ill.

[73] Assignee: Northern Illinois Research, Inc., Wonder Lake, Ill.

[21] Appl. No.: 790,797

[22] Filed: Apr. 25, 1977

Related U.S. Application Data

[63] Continuation of Ser. No. 600,847, Jul. 31, 1975, abandoned.

[51] Int. Cl.² .............. F23H 9/00; F23H 11/24; F24B 1/08; C08K 5/16
[52] U.S. Cl. .................. 128/156; 128/283; 260/33.4 R; 260/874; 260/901
[58] Field of Search .......... 128/155, 156, 283, 296; 260/33.4 R, 874, 901

[56] References Cited

U.S. PATENT DOCUMENTS

| | | | |
|---|---|---|---|
| 2,584,540 | 2/1952 | Botvin et al. | 128/283 |
| 2,702,796 | 2/1955 | Fine | 260/33.4 R |
| 2,780,610 | 2/1957 | Barber et al. | 260/33.4 R |
| 2,832,747 | 4/1958 | Jackson | 260/901 |
| 2,869,548 | 1/1959 | Mason | 128/283 |
| 2,971,510 | 2/1961 | Berger | 128/283 |
| 3,220,960 | 11/1965 | Wichterle | 128/155 |
| 3,283,757 | 11/1966 | Nelsen | 128/283 |
| 3,302,647 | 2/1967 | Marsan | 128/283 |
| 3,307,544 | 3/1967 | Gander et al. | 128/155 |
| 3,494,450 | 2/1970 | Gross | 260/33.4 R |
| 3,502,149 | 3/1970 | Pence, Jr. | 260/33.4 R |
| 3,520,301 | 7/1970 | Fenton | 128/283 |
| 3,547,950 | 12/1970 | Gander | 260/33.4 R |
| 3,624,018 | 11/1971 | Eilers et al. | 260/33.4 R |
| 3,640,741 | 2/1972 | Etes | 128/283 |
| 3,649,574 | 3/1972 | Cole | 260/33.4 R |
| 3,736,934 | 6/1973 | Hennessy | 128/283 |
| 3,763,071 | 10/1973 | Katzer et al. | 260/33.4 R |
| 3,877,431 | 4/1975 | Kross | 128/283 |
| 3,897,781 | 8/1975 | Marsan | 128/283 |
| 3,980,084 | 9/1976 | Kross | 128/283 |

Primary Examiner—Robert W. Michell
Assistant Examiner—V. Millin
Attorney, Agent, or Firm—Emrich, Root, O'Keeffe & Lee

[57] ABSTRACT

A plastic composition adapted for use in contact with the skin, especially in the form of a pad applied to the skin, is manufactured by reacting a mixture of acrylamide-beta methacryloxyethyltrimethylammonium methyl sulfate copolymer, up to about 10 parts of acrylamide-sodium acrylate copolymer per part of said acrylamide-beta methacryloxyethyltrimethylammonium methyl sulfate copolymer, said acrylamide-sodium acrylate copolymer containing up to about 4% of sodium acrylate, and ethylene glycol in an amount sufficient to form a semisolid gel, said proportions being by weight. Useful embodiments of the pad include a sealing pad for an ostomy appliance and a skin-covering pad incorporated in a bandage.

17 Claims, 4 Drawing Figures

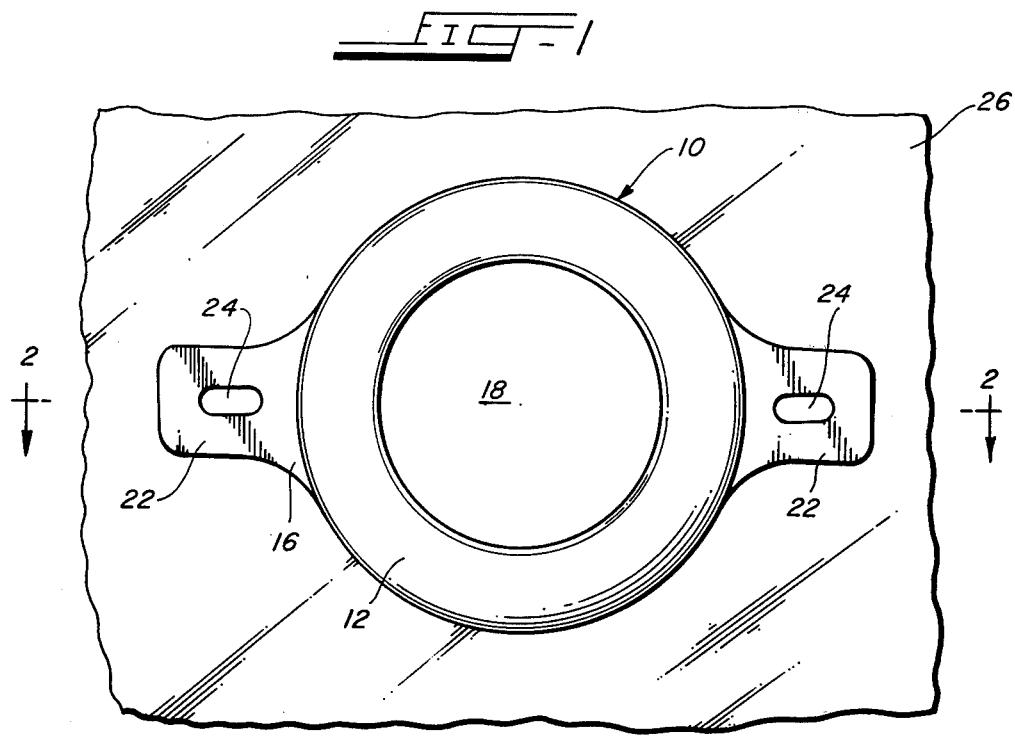
FIG-1
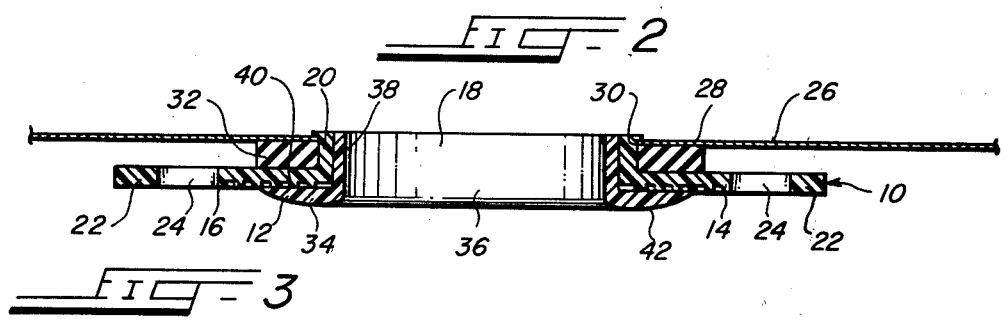
FIG-2
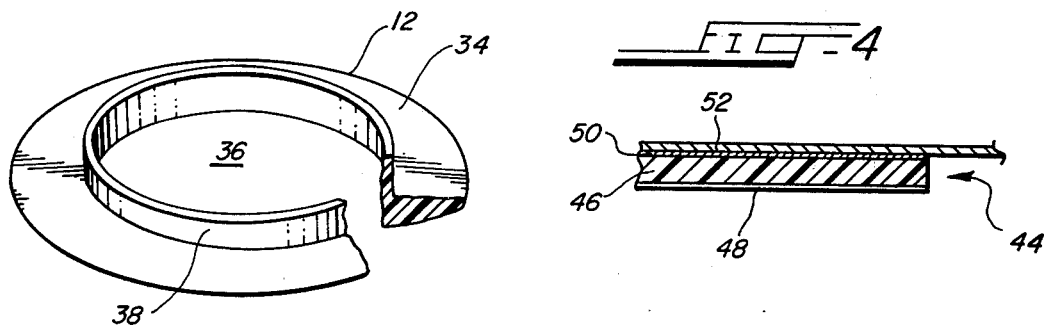
FIG-3
FIG-4

PLASTIC COMPOSITION MANUFACTURE THEREOF, AND PAD FORMED THEREWITH

This is a continuation, of application Ser. No. 600,847, filed July 31, 1975 now abandoned.

BACKGROUND OF THE INVENTION

This invention relates to plastic compositions adapted for use in contact with the skin, to the manufacture thereof, and to articles formed therewith. More particularly, the invention relates to a plastic composition formed as a pad for application to the skin, especially, which may be formed as a sealing pad for an ostomy appliance and which also has other applications.

Certain abdominal surgery, such as colostomy, ileostomy, ureterostomy and the like, results in an opening in the abdominal wall from which extends a stoma for drainage of the interior of the abdominal cavity. A drainage appliance is employed to contain the waste discharged from the body, and it includes a face plate or ring surrounding the stoma and having a drainage pouch or bag mounted thereon to receive the waste. The appliance is supported on the wearer by a belt or strap. A sealing pad or gasket in the form of a ring is employed between the skin of the wearer and the face plate, to prevent leakage and keep the toxic fluids off of adjacent surfaces of the body, and to hold the appliance in place.

While several materials have been employed for forming the sealing pad of an ostomy appliance, pads based upon the inclusion of karaya powder currently are used widely. Such a pad is disclosed in U.S. Pat. No. 3,302,647. Karaya has certain disadvantages, however. It is a nutrient substance which is capable of supporting the growth of microorganisms, not only in use, but when contaminated in storage prior to use. Karaya compositions are lacking in cohesiveness and, therefore, may break down in pieces, which may plug the valve employed at the bottom of the drainage pouch where employed in some instances. Also, it is difficult to form a sealing pad in a shape other than a flat ring. Karaya compositions become slippery when wet, so that a special adhesive may be needed to keep the sealing pad from sliding around and leaking. Karaya is not readily washed off of the skin, but requires scraping for its removal.

In U.S. Pat. No. 3,640,741, I have disclosed a plastic composition suitable for use in a sealing pad for an ostomy appliance, prepared by reacting carboxymethyl cellulose gum or alginate gum with a polyol to form a plastic gel. The carboxymethyl cellulose gum product does not support bacteria growth, and the alginate gum product supports only very little bacteria growth. The preferred materials, however, become slippery when wet, and the materials may break up in pieces, which fall into the drainage pouch. Other characteristics of the compositions of the latter patent could be improved to advantage.

SUMMARY OF THE INVENTION

The invention relates to a novel plastic composition adapted for use in contact with the skin and to the manufacture thereof, such composition being produced by reacting a mixture of acrylamide-beta methacryloxyethyltrimethylammonium methyl sulfate copolymer, up to about 10 parts of acrylamide-sodium acrylate copolymer per part of said acrylamide-beta methacryloxyethyltrimethylammonium methyl sulfate copolymer said acrylamide-sodium acrylate copolymer containing up to about 4% of sodium acrylate, and ethylene glycol in an amount sufficient to form a semisolid gel, said proportions being by weight. The invention also provides a pad adapted for application to the skin and formed of the new composition.

The composition of the invention is especially adapted for use in forming a sealing pad for an ostomy appliance, in the shape of a ring having a central opening for inserting a surgical stoma therethrough, the ring being adapted to be disposed between the skin and an ostomy appliance to provide a seal therebetween.

The new composition is advantageous for use in a sealing pad, and also for use in other applications, in that it does not support the growth of microorganisms, but is a non-nutrient material. Consequently, an article formed of the composition does not become contaminated by microorganism growth during storage or when employed on the body, especially when employed as a sealing ring adjacent to a stoma opening.

The composition has the unique properties of tackifying when wetted, and then remaining tacky and possessing good adhesive properties as it dissolves. Such properties are advantageous in a sealing pad for an ostomy appliance, inasmuch as they act to provide a continuing seal between the appliance and the skin, and the appliance is secured in place to minimize movement thereof around the stoma.

Another advantageous property of the new composition is its cohesiveness. This property enables the composition to be molded in preferred shapes without breaking apart in use. Rather, a sealing pad formed of the composition gradually dissolves in contact with body fluids. The sealing pad lasts substantially longer than the above-described prior sealing pads. The new composition is relatively soft and resilient, minimizing discomfort to the wearer of an ostomy appliance. Material adhering to the skin or to clothing after use is easily removed by washing with soap and water.

Articles formed of the new composition have a long shelf life, in contrast to karaya products, which have but a limited shelf life, hardening during storage.

The foregoing properties of the new composition render it useful in other pads applied to the skin. Thus, it is advantageous to incorporate in a bandage a pad formed of the composition, for contacting and covering an area of the skin. The pad is adapted to maintain cleanliness, in view of its lack of support for microorganism growth. Its adhesiveness serves to retain it in place. The pad both covers the area and affords protection against physical contacts therewith. When it is desired to change the bandage, the outer portion of the pad may be pealed off, to leave in place the portion which adheres to the skin, without disturbing the surface of the skin. When it is desired to remove the remainder of the pad, it may be washed off.

BRIEF DESCRIPTION OF THE DRAWINGS

The attached drawings illustrate preferred embodiments of the invention, without limitation thereto. In the drawings, like elements are identified by like reference symbols in each of the views, and:

FIG. 1 is a fragmentary elevational view of an ostomy appliance having a sealing pad of the invention thereon;

FIG. 2 is a cross sectional view of the appliance and the sealing pad, taken on line 2—2 of FIG. 1;

FIG. 3 is a perspective view, partly broken away and in section, of the sealing pad; and FIG. 4 is a fragmentary sectional view of a bandage in which a pad according to the invention is incorporated.

DESCRIPTION OF THE PREFERRED EMBODIMENTS

Referring to the drawings, FIGS. 1 and 2 illustrate an ostomy appliance 10 of a type disclosed in greater detail in my application for United States Letters Patent, Ser. No. 600,845, filed July 31, 1975, and which includes an annular sealing pad 12 formed of the plastic composition of the invention, described hereinafter. The appliance 10 includes an annular face plate or retainer 14 of relatively stiff and hard material, such as plastic. The retainer includes a flat disc-like annular body 16 having a central circular opening 18 therethrough. A circular flange 20 is integral with the body 16 and extends laterally outwardly therefrom around the inner periphery thereof. Two generally rectangular, flat ears 22 are integral with the body 16 and extend radially therefrom in diametrically opposed relation. Each of the ears is provided with an elongated slot 24, for attachment to the connecting pins of a belt or strap, not shown, by means of which the appliance 10 is supported on the body of the user.

A drainage pouch or bag 26, shown only fragmentarily, is supported on the appliance 10, for collecting waste discharged from the body. The pouch 26 includes a back panel 28 having a circular opening 30 which registers with the flange 20. The back panel 28 is secured to the face plate 14 therearound by an elastomeric adhesive ring 32. Opposite sides of the ring 32 adhere to the body 16 and to the back panel 28, respectively, and the inner periphery of the ring 32 adheres to the flange 20. The appliance is constructed in this manner for arranging the body 16 of the face plate 14 adjacent to the body of the user, with a surgical stoma inserted through the opening 18 in the plate and beyond the back panel 28, for drainage into the pouch 26.

The sealing pad or gasket 12 is interposed between the face plate 14 and the skin of the user surrounding the stoma. The sealing pad 12 serves to contain the waste fluids, which are highly irritating to the skin and contain microorganisms of the intestinal tract, and which also give off offensive odors. Additionally, the sealing pad 12 assists in retaining the appliance 10 in place and makes the appliance more comfortable to wear.

The sealing pad 12 of the invention is especially adapted for performing the foregoing functions. Owing to its composition, the pad 12 may be cast in any desirable configuration, and it will retain its shape and not break apart in use. Referring to FIGS. 1-3, the sealing pad 12 in a preferred embodiment of the invention includes an annular disc-like body 34 defining a central circular opening 36 in the pad, and a circular tubular rim or flange 38 integrally formed in one piece with the body 34 around the inner periphery thereof at the central opening 36 and projecting laterally outwardly therefrom. One surface 40 of the body 34 which is adjacent to the rim 38 is substantially flat and lies in a plane substantially perpendicular to the axis of the rim. The surface 42 on the opposite side of the body 34 diverges inwardly from the flat surface 40 and is slightly rounded or curved.

The rim 38 of the sealing pad 12 has an outer diameter which preferably is approximately the same as but may be less than the inner diameter of the face plate flange 20, for insertion of the rim through the face plate opening 18. The body 34 of the sealing pad 12 overlies the body 16 of the face plate 14. In this manner, the body 34 of the sealing pad 12 is disposed between the user's skin in the area surrounding the stoma, and the face surface of the face plate 14, particularly the surface of its body 16. The rim 38 of the sealing pad 12 extends through the face plate 14 and is disposed between the stoma and the face plate, particularly the flange 20 of the latter. The body 34 of the sealing pad 12 is pressed against the skin area around the stoma, forming a seal around the stoma. The rim 38 assists in forming a seal and also protects the stoma from abrasion and bruising caused by contact with the face plate 14, particularly in the area of the flange 20 and the junction of the flange and the body 16 thereof.

In use, the sealing pad 12 preferably is wetted lightly with water, and the water is blotted off of the pad, to tackify the pad. The pad then adheres readily to the skin of the user, and also to the face plate 14. The sealing pad 12 assists in maintaining the skin area around the stoma in a clean and sanitary condition, with minimal irritation. These results are obtained by virtue of the good adhesion of the sealing pad, forming an effective seal over a relatively long period of time and holding the appliance 10 in place, the non-toxic nature of the pad material, and the non-nutrient nature of the pad material. The sealing pad 12 is soft and resilient, so that the appliance 10 becomes relatively comfortable to wear. The sealing pad 12 is gradually dissolved by the fluids from the stoma, and it is replaced as it begins to lose its effectiveness. The pad does not break apart and deposit particles in the drainage pouch 26, such as occurred with prior sealing pads.

Referring to FIG. 4, a bandage 44 in a preferred embodiment of the invention includes a covering pad or layer 46 of the new plastic composition, a fabric backing sheet 48 embedded in the pad 46 adjacent one surface thereof, a layer 50 of a medical adhesive on the opposite surface of the pad, and a release sheet 52 on the adhesive layer 50. The backing sheet 48 is embedded in the pad 46 during formation of the pad, as by casting or molding, prior to reaching the gel state of the pad composition. Any suitable material may be employed, and representative materials include lightweight high-density polyethylene and polypropylene netting, such as is commercially available as Delnet plastic netting (Hercules Incorporated). The layer 50 may be formed of an adhesive conventionally employed for this purpose. Also, when the pad 46 becomes moist, its surface becomes tacky and binds the pad to the skin. The release sheet 52 may be any suitable sheet material, as conventionally employed for that purpose.

The bandage 44 is used by removing the release sheet 52, placing the adhesive layer 50 against the skin surface to be covered, and pressing on the backing sheet 48 to cause the bandage to adhere to the skin. The skin area then is well-covered and protected from contamination and from physical contacts. When it is desired to remove the covering pad 46, the bulk of the pad may be removed by peeling it off, by pulling on the backing sheet 48, leaving a layer of the pad 46 adhered to the skin. This layer may be permitted to remain on the skin, so as not to disturb the surface. Alternatively, the remaining layer may be removed readily by washing with soap and water.

The plastic composition of the invention is a semisolid gel product of the reaction of at least one acrylic polymer and preferably two acrylic polymers, and ethylene glycol. The preferred polymer is a copolymer of acrylamide and beta methacrylyloxyethyltrimethylammonium methyl sulfate (hereinafter referred to at times by the abbreviation MTMMS) as the quaternizing agent. Preferably, the copolymer contains about 10–40% by weight of MTMMS, corresponding to a molar proportion of about 3–12%, and the balance acrylamide. In a further preferred embodiment, the copolymer contains about 14–23% by weight of MTMMS, corresponding to a molar proportion of about 3–6%.

Preferred copolymers include Reten 210 and Reten 220 high molecular weight cationic water-soluble polymers (Hercules Incorporated). The polymers have molecular weights on the order of about 5–10 million, and they are supplied as finely divided powders, having a screen analysis of 99% through Sieve No. 40 of the U.S. Sieve Series. Reten 210 contains about 14–23% by weight of MTMMS, corresponding to about 3–6 mole percent of the monomer, and the balance acrylamide. The polymer has a solution viscosity of 600–1,000 centipoises (viscosities determined in 1% aqueous solution at 25° C., Brookfield LVF, 30 rpm.). Reten 220 contains 30–40% by weight of MTMMS monomer, corresponding to 8–12 mole percent, and the balance acrylamide. Its solution viscosity is 800–1,200 centipoises.

It is preferred that acrylamide-sodium acrylate copolymer also be included in the reaction mixture employed for making the new plastic composition. The acrylamide-sodium acrylate copolymer may contain up to about 4% an acrylate salt such as sodium acrylate, which results from hydrolysis during the polymerization of acrylamide. The acrylamide-sodium acrylate copolymer is employed in a proportion up to about 10 parts per part of the copolymer, acrylamide-MTMMS, in parts by weight. Preferably, acrylamide-sodium acrylate copolymer is employed in a weight ratio to the acrylamide-MTMMS copolymer of about 4–9:1.

A preferred commercially available acrylamide-sodium acrylate copolymer product in Reten 420, an essentially non-ionic water-soluble acrylamide-sodium acrylate copolymer having an estimated sodium acrylate content resulting from hydrolysis of about 2–4% by weight, and a molecular weight on the order of 5–10 million. The product is supplied as a powder, of which 99% passes through Sieve No. 20 of the U.S. Sieve Series. The polymer has a solution viscosity of 300–500 centipoises (1% aqueous solution at 25° C., Brookfield LVF, 60 rpm.).

Ethylene glycol is incorporated in the reaction mixture in an amount sufficient to form a semisolid gel. Preferrably the ethylene glycol is present in a weight proportion of about 2–5 parts per part to the polymers present in the reaction mixture, i.e., the total of acrylamide-MTMMS copolymer and acrylamide-sodium acrylate copolymer. Preferably the weight proportion of ethylene glycol is about 4–50 parts per part of acrylamide-MTMMS, copolymer.

Reaction of the mixture of polymer or polymers and ethylene glycol occurs spontaneously at room temperature, or about 22° C., under substantially anhydrous conditions. As illustrated in the examples, a semisolid gel forms under such conditions in about 30–60 minutes. The gel formed in this manner has the above-described properties which are advantageous for forming a pad for application to the skin. The composition may be formed into a desired shape by casting or injection molding.

A shaped composition formed by the inclusion of both acrylamide-MTMMS copolymer and polyacrylamide in the reaction mixture has a body and resiliency similar to silicone rubber. The composition is denser than the above-described prior materials employed for like purposes, affording more versatility in molding desired shapes. A shaped composition formed by the sole inclusion of the acrylamide-MTMMS copolymer, i.e., omitting the polyacrylamide, has less body and elasticity, and is more putty-like. The latter composition also dissolves more rapidly.

The rate of gel formation may be regulated by cooling during the reaction, if desired. A more rigid, less resilient composition may be produced by conducting the reaction under higher temperature and pressure, for example, in an autoclave indirectly heated by steam at 15 p.s.i.g.

Medicaments, microbicides, and the like may be incorporated in the reaction mixture. In forming the bandage 44 of FIG. 4, the reaction mixture is cast on or molded on the backing sheet 48.

The following examples are furnished to illustrate the invention. The invention is not limited to the examples or to the materials, proportions, conditions and procedures employed therein, which are merely illustrative.

EXAMPLE 1

Reten 210 and Reten 420, acrylic polymers in powder form and having the above-described compositions, are employed in the manufacture of the new plastic composition. 24 grams of Reten 210 and 126 grams of Reten 420 are well-mixed. A 537-gram quantity of ethylene glycol is added to the mixture of polymers with the materials initially at room temperature, and the materials are mixed for several minutes under substantially anhydrous conditions, until smooth and pourable. The fluid mixture is poured into a mold or onto a casting sheet, where an exothermic reaction takes place. The mixture is allowed to react under ambient conditions, and gel formation takes place. A semisolid or thick gel forms in about 30 minutes. The resulting composition may be sterilized with cobalt (60) radiation, ethylene oxide, or autoclaving. The composition may be employed thereafter in the form of a pad or the like in contact with the skin, particularly, in the form of a sealing pad for an ostomy appliance, or in the form of a bandage pad, as described above.

EXAMPLE 2

A composition was prepared as described in Example 1 from Reten 210 and Reten 420. The Reten 210 contained 18.4% by weight of MTMMS and the balance copolymerized acrylamide. The Reten 420 on analysis was found to contain 0.32% sodium present as sodium acrylate, the balance being copolymerized acrylamide.

The composition was employed in eye irritation and primary skin irritation tests conducted on albino rabbits and patterned after the methods of Draize et al, "Methods for the Study of Irritation and Toxicity of Substances Applied Topically to the Skin and Mucous Membranes", *J. Pharm. & Exp. Ther.*, 82, 377 (1944). The eye irritation test employed also is described in U.S. Pat. No. 3,640,741. The descriptive rating system for the degree of irritation in the respective tests was as follows:

| Eye Irritation | Skin Irritation |
|---|---|
| Extreme | Extreme |
| Severe | Severe |
| Moderate | Moderate |
| Mild | Mild |
| Minimal | Slight |
| Practically None | Minimal |
| None | None |

The irritation resulting from use of the composition tested was rated minimal in each of the tests.

EXAMPLE 3

Reten 210 alone, or Reten 210 and Reten 420 together, employed in powder form, and ethylene glycol are mixed and reacted in the manner of Example 1. The materials, proportions, and approximate time required to produce a semisolid or thick gel suitable for use in the form of a pad such as an ostomy appliance sealing pad or a bandage pad are as follows:

| Reten 210 grams | Reten 420, grams | Ethylene Glycol, grams | Gel Time, minutes |
|---|---|---|---|
| 6 | 54 | 224 | 60 |
| 24 | 108 | 269 | 30 |
| 6 | 54 | 269 | 60 |
| 60 | — | 269 | 30 |

I claim:

1. A process of making a plastic composition adapted for use in contact with the skin which comprises:
reacting a mixture of about one part of acrylamide-beta methacryloxyethyltrimethylammonium methyl sulfate copolymer, and up to about 10 parts of acrylamide-sodium acrylate copolymer per part of said acrylamide-beta methacryloxyethyltrimethylammonium methyl sulfate copolymer, said acrylamide-sodium acrylate copolymer containing about 1% to about 4% by weight of sodium acrylate;
said acrylamide-beta methacryloxyethyl-trimethylammonium methyl sulfate copolymer containing about 14% to 40% by weight of said sulfate with the balance being acrylamide; and
about 2 to 5 parts by weight of ethylene glycol per part of the said copolymers combined to form a gel.

2. A process as defined in claim 1 and wherein said acrylamide-sodium acrylate copolymer is present in a weight proportion of about 4–9 parts per part of said acrylamide-beta methacryloxyethyltrimethylammonium methyl sulfate copolymer.

3. A plastic composition adapted for use in contact with the skin and produced by the process of claim 2.

4. A plastic composition adapted for use in contact with the skin and produced by the process of claim 1.

5. A pad adapted for application to the skin and formed of the composition of claim 4.

6. An annular sealing pad for an ostomy appliance formed of the composition of claim 4, having a central opening for inserting a surgical stoma therethrough, and being adapted to be disposed between the skin and an ostomy appliance to provide a seal therebetween.

7. A sealing pad as defined in claim 6 and having an annular disc-like body for disposition between the skin and the surface of an annular face plate in said appliance, and a rim integrally formed in one piece with said body around the inner periphery thereof and projecting outwardly therefrom through the face plate for disposition between the stoma and the face plate.

8. In a bandage for application to the skin, a pad formed of the composition of claim 4 arranged for contacting and covering an area of the skin.

9. A process in accordance with claim 1 in which:
said ethylene glycol is present in a weight proportion of about 4–50 parts per part of said acrylamide-beta methacryloxyethyltrimethylammonium methyl sulfate copolymer.

10. A process of making a plastic composition adapted for use in contact with the skin and characterized by becoming tacky upon being wetted which comprises:
reacting about one part of an acrylic polymer having a molecular weight of about 5 to 10 million of the group consisting of a water-soluble copolymer of acrylamide and a quaternizing agent and a mixture of a water-soluble copolymer of acrylamide and a quaternizing agent and a water-soluble copolymer of acrylamide and an acrylate salt with about 2 to 5 parts of ethylene glycol per part of said polymer or mixture of polymers to form a gel, said reaction taking place in no more than about one hour at ambient temperature.

11. A process of making a plastic composition in accordance with claim 10 in which:
said acrylic polymer is a water-soluble copolymer of acrylamide and a quaternizing agent.

12. A process of making a plastic composition in accordance with claim 10 in which:
a mixture of a water-soluble copolymer of acrylamide and a quaternizing agent and a water-soluble copolymer of acrylamide and an acrylate salt is used.

13. A process of making a plastic composition in accordance with claim 10 in which:
said water-soluble copolymer of acrylamide and a quaternizing agent contains about 10%–40% by weight of beta methacryloxyethyltrimethylammonium methyl sulfate as said quaternizing agent.

14. A process of making a plastic composition in accordance with claim 10 in which:
said water-soluble copolymer of acrylamide and an acrylate salt contains about 1% to 4% by weight of sodium acrylate as said salt.

15. A process of making a plastic composition in accordance with claim 10 in which:
a mixture of about one part of a water-soluble copolymer of acrylamide and a quaternizing agent and about 4 to 9 parts of a water-soluble copolymer of acrylamide and an acrylate salt is used to form an ostomy appliance.

16. A plastic composition prepared by the process of claim 10.

17. A process of making a plastic composition in accordance with claim 10 in which:
said acrylic polymer is a water-soluble copolymer of acrylamide and an acrylate salt.

* * * * *

UNITED STATES PATENT OFFICE
CERTIFICATE OF CORRECTION

Patent No. 4,153,055            Dated May 8, 1979

Inventor(s) Donald E. Etes

It is certified that error appears in the above-identified patent and that said Letters Patent are hereby corrected as shown below:

Col. 3, line 12: after "July 31, 1975," insert-- now U.S. Patent No. 4,054,140,--;

Col. 5, line 34: after "4%" insert--by weight of--;

Col. 6, line 5 and 6: delete "polyacrylamide" and insert-- acrylamide-sodium acrylate copolymer--; and line 12: delete "polyacrylamide" and insert-- acrylamide-sodium acrylate copolymer--.

Signed and Sealed this

Twenty-fourth Day of July 1979

[SEAL]

Attest:

Attesting Officer

LUTRELLE F. PARKER
Acting Commissioner of Patents and Trademarks